United States Patent [19]

Lefebvre

[11] Patent Number: 5,146,937
[45] Date of Patent: Sep. 15, 1992

[54] METHOD OF HAIR HIGHLIGHTING USING POLYSTYRENE SHEET

[76] Inventor: Stéphane Lefebvre, 3556, Clark Street, Montréal, Québec, Canada, H2X 2R8

[21] Appl. No.: 764,209

[22] Filed: Sep. 23, 1991

[51] Int. Cl.⁵ .............................................. A61K 7/13
[52] U.S. Cl. .................................... 132/208; 132/222
[58] Field of Search ............... 132/200, 207, 208, 222, 132/270

[56] References Cited

U.S. PATENT DOCUMENTS

| | | | |
|---|---|---|---|
| 3,465,759 | 9/1969 | Haefele | 132/207 |
| 3,691,270 | 9/1972 | Charle et al. | 132/320 X |
| 4,672,983 | 6/1987 | Nath et al. | 132/208 |

*Primary Examiner*—John J. Wilson
*Assistant Examiner*—Jeffrey A. Smith
*Attorney, Agent, or Firm*—Pierre Lespérance; Francois Martineau

[57] ABSTRACT

The use of a sheet made of a polymer material, preferably polystyrene, having semi-flexible, thermally-insulating, hair-clinging, non porous, non slipping properties, as a dye-applying pad for hair highlighting. The polystyrene sheet defines one and another opposite flat portions merging about a fold line. A lock of hair is laid over one flat half portion of the sheet, and a fluid (e.g. gel, cream, or cream gel) dye solution including oxidizing means is applied to the lock of hair. The other flat half portion of the sheet then folded over and flatly compressed against the first portion of sheet to take the locks in sandwich for a sufficient development time to enable permanent hair coloring.

2 Claims, 1 Drawing Sheet

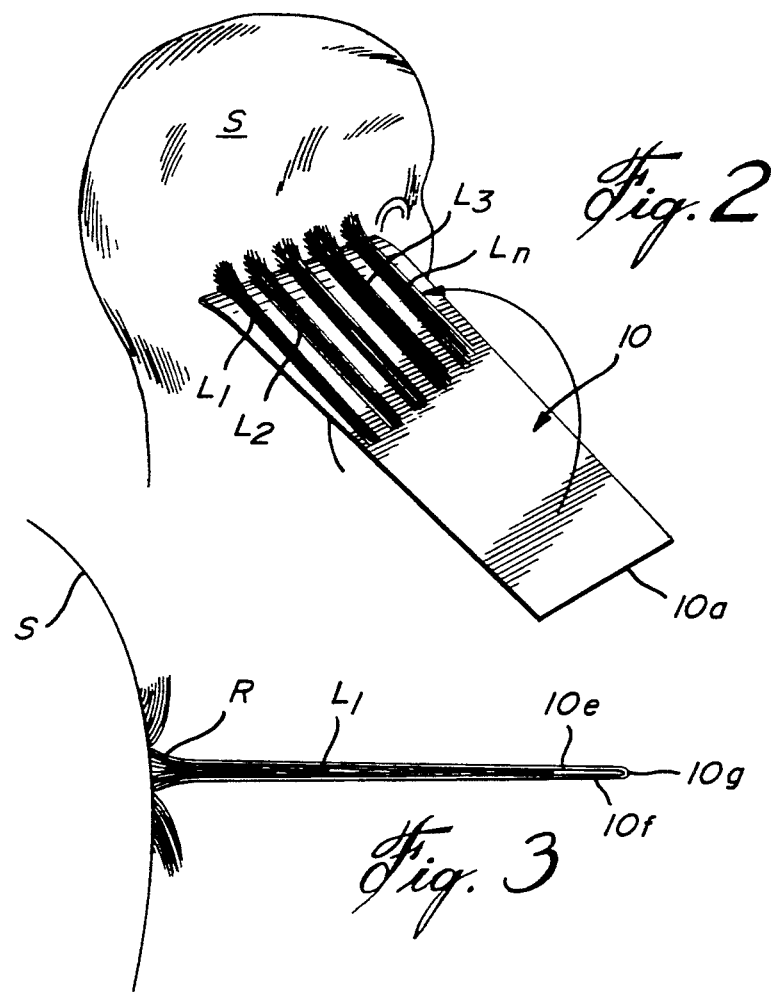
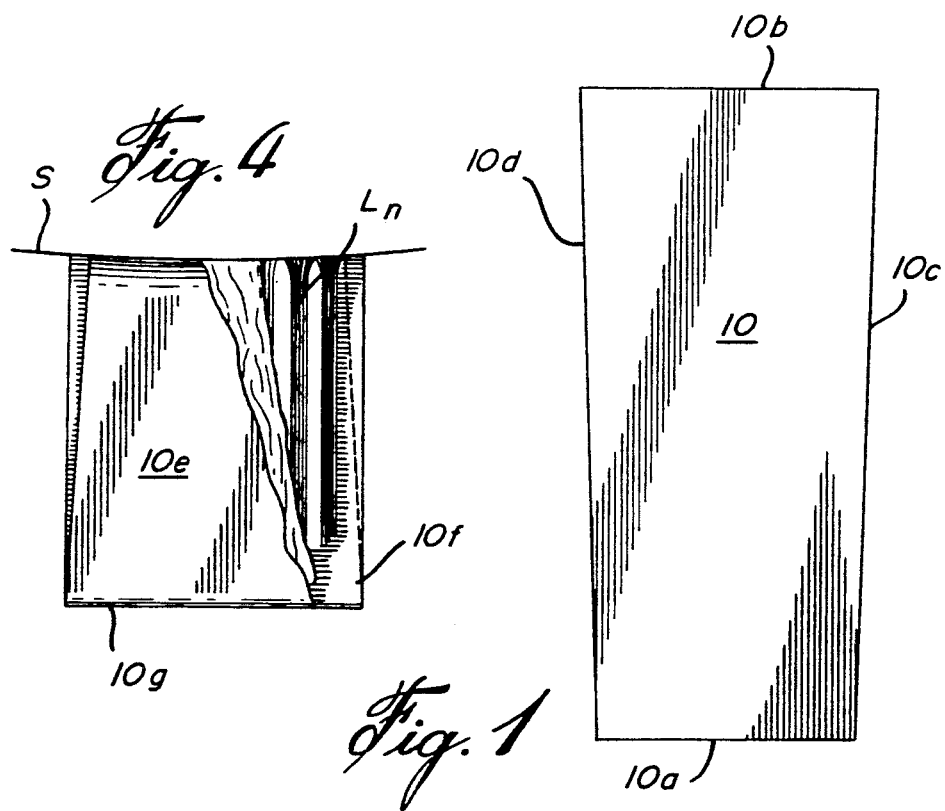

METHOD OF HAIR HIGHLIGHTING USING POLYSTYRENE SHEET

FIELD OF THE INVENTION

The invention relates to the hairdressing trade, particularly to the technique known as hair highlighting.

BACKGROUND OF THE INVENTION

Hair dyeing conventionally includes the use of a rectangular aluminum foil or other plastic material, as a flat support for a lock of hair to be selectively colored, as means to enclose the lock by the folding in two of the aluminum foil in view of enclosing and containing the bleach or dye fluid applied to the lock, and as a compression pad to maintain the dye fluid over each hair strand of the lock. The foil is usually positioned transversely of the scalp to edgewisely abut against the scalp. Thus, substantially all the length of each hair strand of that lock will come in contact with the dye fluid. Such a technique of selective coloring of a lock is known in the trade as hair highlighting.

Since the dye fluid, which may consist of a gel, or cream, usually includes a liquid coloring ingredient combined with an oxidizer, usually peroxide ($H_2O_2$), it is desirable to prevent the dye fluid from engaging the scalp. Therefore, because of the high flexibility of the rectangular aluminum sheet material, each of the two opposite pairs of overlapping lateral side edge portions of the folded sheet must be edgewisely folded onto themselves, to "close" both lateral side edges of the folded sheet. This is required, because additional structural rigidity to the folded sheet must be provided, dye leakage must be prevented, and each colored lock must be isolated from the remaining hair. This edgewise folding is also required because aluminum has a somewhat slippery surface, therefore the aluminum foil would otherwise slip and slide off the hair during the hour-long development time.

OBJECTS OF THE INVENTION

The general object of the invention is to provide a polystyrene sheet to replace the usual aluminum foil as a dye applying compression pad during the hair highlighting technique, so as to enable faster and easier use relative to aluminum foil.

An additional object of the invention is to enable improved monitoring of the development time of the hair highlighting.

An object of the invention is to improve the adherence of hair strands on the highlighting compression pad.

An object of the invention is to waive the requirement, during highlighting, of applying an external heat source to the compression pad, thanks to the insulating features of polystyrene as the constituting material of the compression pad.

An object of the invention is to provide a compression pad for hair highlighting, which, while remaining flexible, is somewhat more rigid than conventional aluminium foils, so that it would not be necessary anymore to fold onto themselves each pair of opposite lateral side edges of the folded sheet during highlighting.

A corollary object of the invention is to render the compression pad be reusable, for several times, since a crumpled polystyrene sheet will automatically return substantially to its uncrumpled state after use (up to a certain point) contrarily to aluminum foil.

SUMMARY OF THE INVENTION

Accordingly with the objects of the invention, there is disclosed a sheet made of a polymer material having semi-flexible, thermally insulating, hair lock clinging, non-porous, non-slippery properties, for use as a dye-applying pad for hair highlighting coloring, said sheet being continuous and flat and defining one and another opposite flat portions merging about a fold line, a few locks of hair destined to be laid onto said sheet one portion, and a fluid dye solution including oxidizing means destined to be applied over said sheet one portion, and said sheet another portion to be thereafter folded over and flatly compressed against said sheet one portion to take said locks of hair in sandwich for a sufficient development time for permanent hair coloring.

BRIEF DESCRIPTION OF THE DRAWINGS

FIG. 1 is a plan view of a quadrangular sheet of polystyrene according to the invention;

FIG. 2 is a perspective view of the polystyrene sheet of FIG. 1, supporting on one half portion locks of hair depending from a person's scalp;

FIG. 3 is an edge view of the polymer sheet of FIG. 1, shown folded in two and taking in sandwich the lock; and FIG. 4 is a partly broken plan view of the folded polymer sheet of FIG. 3.

DETAILED DESCRIPTION OF THE INVENTION

Polystyrene is the choice material for use in the present invention as the compression pad in the hair highlighting technique. Polystyrene (PS), a colorless, translucent plastic, is by definition a polymer of styrene. The chemical formula of PS is $(C6H5CHCH_2)_n$.

Quadrangular polymer sheet, namely, PS sheet 10, forms a flat, flexible, plastic strip. PS sheet 10 preferably defines two elongated, opposite edges 10c, 10d and two short edges 10a, 10b. Preferably, sheet 10 increases progressively in width from one small edge 10a to the opposite edge 10b, so that edge 10b is longer than edge 10a. The thickness of sheet 10 is preferably approximately constant, advantageously being less than 250 microns, and preferably in the range of 115 to 165 microns.

In operation, a few locks, $L_1, L_2, L_3, \ldots L_n$ (n being small) are manually lifted from a common area of scalp S i.e. pivoted about their scalp embedded roots R, and laid over the flat, wider, underlying half portion 10b of polymer sheet 10. Sheet elongated edge 10b is then brought to bear against scalp S. Sheet portion 10e need not be maintained in horizontal position. The fluid dye compound is poured over the locks of hair $L_1, \ldots L_n$ which lay on the sheet surface 10e. The fluid dye conventionally includes a hair coloring ingredient and an oxidizer such as peroxide ($H_2O_2$). The narrower half portion 10e of PS sheet 10 is then folded over the other wider half portion 10f, about fold line 10g, thus taking to forcibly seep sandwich locks $L_1, \ldots L_n$ and thus biasing the dye solution in between each pair of adjacent strands of hair.

PS sheet 10 forms therefore a "microscopic sponge", defining a plurality of non-porous, micro-cavities. These micro-cavities, typical of the polystyrene material used for sheet 10, are engaged by the dye and/or bleach fluid when the latter is spread over the sheet 10. The advantage of these micro-cavities is that the dye/bleach solution does not need to be spread over a horizontally-disposed sheet 10. Indeed, because the fluid will stick to the polystyrene sheet due to the sheet inherent sticky property, the dye fluid can be poured over the sheet 10 even when the sheet 10 is inclined almost at the vertical, and the fluid spread over the sheet 10 will remain on the sheet—it will not fall slopewise of the sheet 10 to the ground. It is understood that this was not the case with conventional aluminum foils, since lateral edge flaps had to be closed to prevent dye/bleach leakage from the foil.

Preferably, sheet 10 is positioned substantially transverse—orthogonally—to the tangential section of scalp to prevent the dye from undesirably staining scalp S. Moreover, care should be taken, during the folding of the PS sheet 10 to take in sandwich the hair locks L, so that the lateral side edges 10c, 10d register with one another, and the end edges 10a, 10b come in substantially exact register with one another. Since sheet flap 10e is narrower than scalp-engaging sheet flap 10f, their lateral side edges 10c, 10d will not come in exact register with one another, but what is important is that both flaps be generally aligned with one another, as suggested in FIG. 4 of the drawings.

It is understood that, due to the inherent thermal insulating capability of PS in the present PS sheet, heat generated as a by-product of the chemical process of oxidation occurring with oxidizer $H_2O_2$ applied onto the locks L and the dye, will be positively trapped and retained within the volume of air defined between the two folded sheet halves 10e, 10f. This in turn waives the usual requirement of periodically submitting the folded dye pad 10e, 10f (during highlighting development time) to an external heat source—a hair dryer e.g.—and promotes better and more efficient monitoring of the effective development time, and therefore, of a more efficient hair highlighting. To verify the developing time, one simply needs to temporarily unfold the folded PS sheet 10e, 10f. Developing time is normally in the range of ten to sixty minutes.

PS as a material is particularly advantageous, in that it enables hair to cling thereto, i.e. to adhere in a releasable but firm fashion. This has to do with its non-porous nature and to the non-slippery dullness of its surface.

Preferably, the PS sheet is made of expanded polystyrene such as the material manufactured and sold by the United States corporation Astro-Valcourt Company limited, of 18 Peck Avenue, Post Office box 148, Glenn Falls, N.Y. 12801.

PS is known for use especially as:

(a) an anti-skid sheet surface, to be installed into a food service tray in commercial airlines and hotels;

(b) as a thermal insulating batt, for building construction;

(c) as a shock-dampening shield, for use in packaging of fragile goods that can become damaged during transportation; and (d) as an easily malleable substance, for use by scupltors, architects, and in industrial manufacturing processes for making molded products.

However, to the knowledge of the present inventor, PS has never been used in the hairdressing trade for use in hair lock highlighting technique. The invention is therefore directed to a novel use of a known material.

I claim:

1. A method for highlighting hair with a quadrangular, planar sheet of expanded polystyrene material, comprising the steps of:
   (a) laying a few locks of a person's hair onto a first half portion of said sheet;
   (b) applying a dye fluid to said locks of hair;
   (c) folding a second half portion of said polystyrene sheet over said sheet first portion, to take in sandwich therebetween said locks of hair;
   (d) applying planar pressure evenly over said sheet folded half portions, to bring said sheet first and second half portions flatly against each other in an operative hair highlighting condition, and to accordingly spread said dye fluid within a generally open pocket defined between the two said sheet half portions;
   (e) releasing said planar pressure in such a way as to allow the locks of hair to adhere to both sheet half portions in a releasable but firm fashion, so as to glue said sheet half portions to one another in their said folded operative condition;
   (f) allowing the assembly of folded polystyrene sheet and glued locks of hair to hang freely from that person's scalp for a controlled dye development period of approximately ten to sixty minutes;
   (g) releasing said sheet second half portion from said sheet first half portion, at the end of said dye development period; and
   (h) releasing said sheet first portion from said locks of hair;

wherein said expanded polystyrene sheet has a thickness ranging between 115 and 250 microns, and defines on its wall a plurality of micro-cavities at least a number of which become filled by said dye.

2. A method as in claim 1,
   further including a step (cc) performed after step (c) and before step (d), and consisting of edgewisely abutting said folded polystyrene sheet against that person's scalp.

* * * * *